United States Patent [19]

Winchel

[11] Patent Number: Plant 6,705

[45] Date of Patent: Mar. 28, 1989

[54] ROSE PLANT

[75] Inventor: Joe Winchel, Harbor City, Calif.

[73] Assignee: Co-Operative Rose Growers, Inc., Tyler, Tex.

[21] Appl. No.: 109,307

[22] Filed: Oct. 16, 1987

[51] Int. Cl.[4] ..... A01H 5/00

[52] U.S. Cl. ..... Plt./11

[58] Field of Search ..... Plt./11

*Primary Examiner*—Robert E. Bagwill

*Attorney, Agent, or Firm*—Vincent G. Gioia

[57] ABSTRACT

A new unusual cardinal red and near white bicolor hybrid tea rose.

1 Drawing Sheet

The present invention relates to a new and distinct variety of rose plant of the hybrid tea rose class, which was originated by my crossing as seed parent and pollen parent two unnamed, unpatented seedlings of my creation. The denomination of this new rose is "Double Perfection".

Among the novel characteristics possessed by this new variety which distinguish it from its parents and all other varieties of which I am aware are its unusual cardinal red and near white bicolored flowers. Its outer petals vary from petal to petal with respect to extent and areas of red coloring. Asexual reproduction by budding of the new variety as performed in Smith County, Tex., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new Royal Horticultural society Colour Chart (R.H.S.C.C.). The variety, with color terminology in accordance with The terminology used in color description herein refers to plate numbers in the aforementioned colour chart, e.g., "51A" is plate 51A of The Royal Horticultural Society Color Chart.

Parentage: Seedling.

*Seed parent.*—Unnamed seedling.

*Pollen parent.*—Unnamed seedling.

Class: Hybrid tea.

The following observations are made of specimens grown outdoors in Smith County, Tex., during the month of June.

FLOWER

Blooming habit: Recurrent.

A. Bud:

(1) *Size.*—Medium.

(2) *Form.*—Pointed.

(3) *Color.*—As sepals first divide, bud color is near Rhodonite Red 51A.

(4) *Sepals.*—Longer than bud, some appendages.

(5) *Peduncle.*—Length — long. Aspect — straight. Strength — erect. Color — near 181C.

B. Bloom:

(1) *Size.*—Average size when fully expanded — about 4½ inches.

(2) *Borne.*—Singly, one to a stem.

(3) *Form.*—High centered. Outer petals reflex and quill to points; inner petals roll under.

(4) *Petalage.*—Number of petals under normal conditions — about 35.

(5) *Color.*—After sepals fall and petals unfurl, color quickly changes to reveal beautiful red and near white bicolored flowers. The red coloring is only in the outer petals and the extent and area of red coloring differs from petal to petal. At their deepest tonality, outer petal can be near cardinal red 53A lightening to near 51A through washing with near white although some petals show clear demarcation of red and white coloring at different locations from petal to petal. Thus, some petals may be almost all red or both red and cream color, near 158D. Inner petals are devoid of red coloring being near 158D at top surfaces and near 158B at undersurfaces. Occasional red coloring may be seen at the top edge of some petals. Both top and undersurfaces also show characterstic veining.

C. Petals:

(1) *Texture.*—Thick.

(2) *Appearance.*—Inside velvety and outside satiny.

(3) *Form.*—Broad, fan shaped with pointed apices.

(4) *Arrangement.*—Regularly arranged.

(5) *Petaloids in center.*—Few.

(6) *Persistence.*—Slight persistence.

(7) *Fragrance.*—Slight.

(8) *Lasting quality.*—Average.

REPRODUCTIVE ORGANS

A. Stamens, filaments and anthers:

*Arrangement and color.*—Regularly arranged around styles. Color — yellow-orange.

B. Pollen:

*Color.*—Yellow.

C. Styles: Medium length.

D. Stigmas:

*Color.*—Cream.

E. Hips: Globular, average size, orange color, some seeds protrude slightly.

PLANT

A. Form: Upright.

B. Growth: Uniform branching.

*Height attained.*—About 4 feet.

C. Foliage: Compound 5 leaflets.

(1) *Size.*—Medium.

(2) *Quantity.*—Abundant.

(3) *Color.*—New foliage: Upper side — near 138A. Under side — near 138B. Old foliage: Upper side — near 147A. Under side — near to 148B.

(4) *Shape.*—Oval, pointed.

(5) *Texture.*—Upper side is semiglossy, slight veining; under side is matte, abundant veining.

(6) *Edge.*—Serrate.

(7) *Serration.*—Ordinary.

(8) *Leaf stem.*—Color — near to 147B. Under side — near 146B.

(9) *Stipules.*—Medium length.

(10) *Resistance to disease.*—Blackspot — good. Mildew — good. Rust — good.

D. Wood:

(1) *New wood.*—Color — near 144B. Bark — smooth.

(2) *Old wood.*—Color — near 144A. Bark — smooth.

E. Thorns:

(1) *Thorns.*—Quantity (main stalk) — ordinary. On laterals from stalk — few. Form — flat base, slight recurve. Length — medium. Color — near 164D. Position — irregular.

F. Winter hardiness: Needs protection in severe climates.

I claim:

1. A new and distinct variety of rose plant of the hybrid tea rose class, substantially as shown and described, characterized particularly by unusual red and near white bicolored flowers.

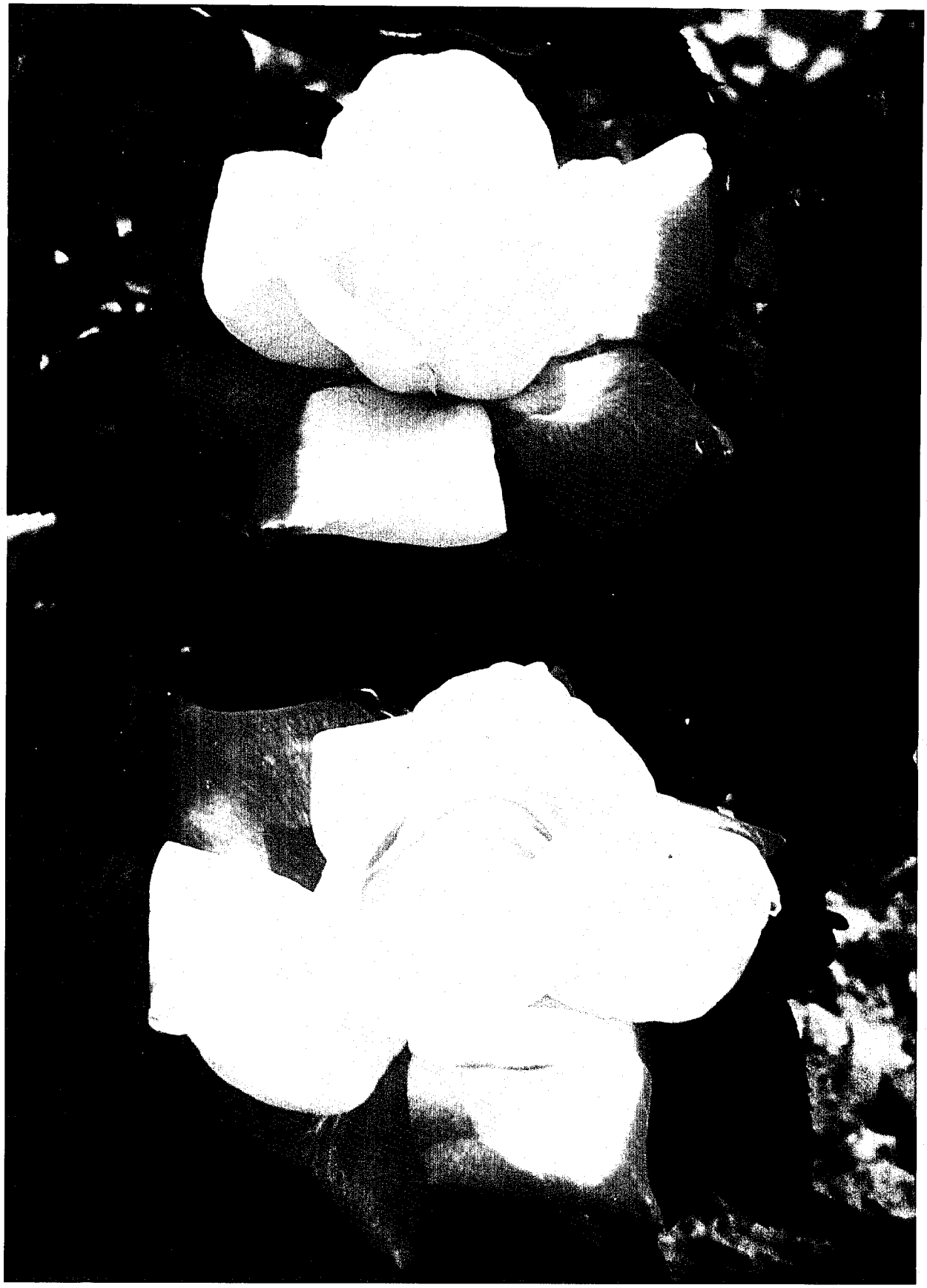

* * * * *